(12) United States Patent
Pinkos et al.

(10) Patent No.: US 8,471,042 B2
(45) Date of Patent: Jun. 25, 2013

(54) METHOD FOR PRODUCING 1,6-HEXANEDIOL AND CAPROLACTONE

(75) Inventors: Rolf Pinkos, Bad Duerkheim (DE); Daniel Breuninger, Bobenheim-Roxheim (DE); Gerd-Dieter Tebben, Mannheim (DE)

(73) Assignee: BASF SE, Ludwigshafen (DE)

( * ) Notice: Subject to any disclaimer, the term of this patent is extended or adjusted under 35 U.S.C. 154(b) by 20 days.

(21) Appl. No.: 13/258,166

(22) PCT Filed: Mar. 31, 2010

(86) PCT No.: PCT/EP2010/054285
§ 371 (c)(1),
(2), (4) Date: Sep. 21, 2011

(87) PCT Pub. No.: WO2010/115798
PCT Pub. Date: Oct. 14, 2010

(65) Prior Publication Data
US 2012/0010419 A1 Jan. 12, 2012

(30) Foreign Application Priority Data
Apr. 7, 2009 (EP) .................. 09157503

(51) Int. Cl.
*C07D 313/00* (2006.01)
*C07C 27/04* (2006.01)

(52) U.S. Cl.
USPC .......................... 549/266; 568/864

(58) Field of Classification Search
USPC .......................... 549/266; 568/864
See application file for complete search history.

(56) References Cited

U.S. PATENT DOCUMENTS

| | | |
|---|---|---|
| 3,933,930 A | 1/1976 | Dougherty et al. |
| 2007/0112225 A1 | 5/2007 | Sirch et al. |
| 2008/0207958 A1 | 8/2008 | Haunert et al. |
| 2010/0168445 A1 | 7/2010 | Pinkos et al. |
| 2010/0240913 A1 | 9/2010 | Pinkos et al. |
| 2010/0256398 A1 | 10/2010 | Pinkos et al. |
| 2011/0015429 A1 | 1/2011 | Pinkos et al. |
| 2011/0124905 A1 | 5/2011 | Pinkos et al. |

FOREIGN PATENT DOCUMENTS

| | | |
|---|---|---|
| DE | 1 235 879 | 3/1967 |
| DE | 1 618 143 | 10/1970 |
| DE | 2 013 525 | 10/1970 |
| DE | 2 060 548 | 6/1972 |
| DE | 2 321 101 | 11/1974 |
| DE | 196 07 954 | 9/1997 |
| DE | 197 38 464 | 3/1999 |
| DE | 10 2004 054 047 | 5/2006 |
| EP | 0 349 861 | 1/1990 |
| WO | 2006 005504 | 1/2006 |
| WO | 2008 152001 | 12/2008 |

OTHER PUBLICATIONS

U.S. Appl. No. 13/381,116, filed Dec. 28, 2011, Kunst, et al.
Musser, M. T., et al., "Cyclohexanol and Cyclohexanone," Ullmann's Encyclopedia of Industrial Chemistry, Fifth Completely Revised Edition, vol. A 8: Coronary Therapeutics to Display Technology, pp. 217-227, (1987).
"Homogen katalysierte Hydrierungen," Methods of Organic Chemistry, vol. IV/1c, pp. 45-67 (1980).
"Heterogen katalysierte Hydrierungen," Methods of Organic Chemistry, vol. IV/1c, pp. 16-29 (1980).
International Search Report Issued Oct. 1, 2010 in PCT/EP10/054285, filed Mar. 31, 2010.
U.S. Appl. No. 13/133,006, filed Jun. 6, 2011, Abillard, et al.
U.S. Appl. No. 13/257,496, Sep. 19, 2011, Pinkos, et al.
U.S. Appl. No. 13/226,049, filed Sep. 6, 2011, Abillard, et al.
U.S. Appl. No. 13/258,207, Sep. 21, 2011, Abillard, et al.

*Primary Examiner* — Nizal Chandrakumar
(74) *Attorney, Agent, or Firm* — Oblon, Spivak, McClelland, Maier & Neustadt, L.L.P.

(57) ABSTRACT

The invention relates to a process for preparing 1,6-hexanediol and caprolactone, preferably with at least 99.5% purity, which are especially virtually free of 1,4-cyclohexanediols, from a carboxylic acid mixture which is obtained as a by-product of the catalytic oxidation of cyclohexane to cyclohexanone/cyclohexanol with oxygen or oxygen-comprising gases and by water extraction of the reaction mixture, by hydrogenating the carboxylic acid mixture, esterifying and hydrogenating a substream to hexanediol and cyclizing 6-hydroxycaproic ester, the 1,4-cyclohexanediols being removed either in the course of fractionation of the esterification mixture or last from the caprolactone.

27 Claims, 3 Drawing Sheets

METHOD FOR PRODUCING 1,6-HEXANEDIOL AND CAPROLACTONE

Figure 1:
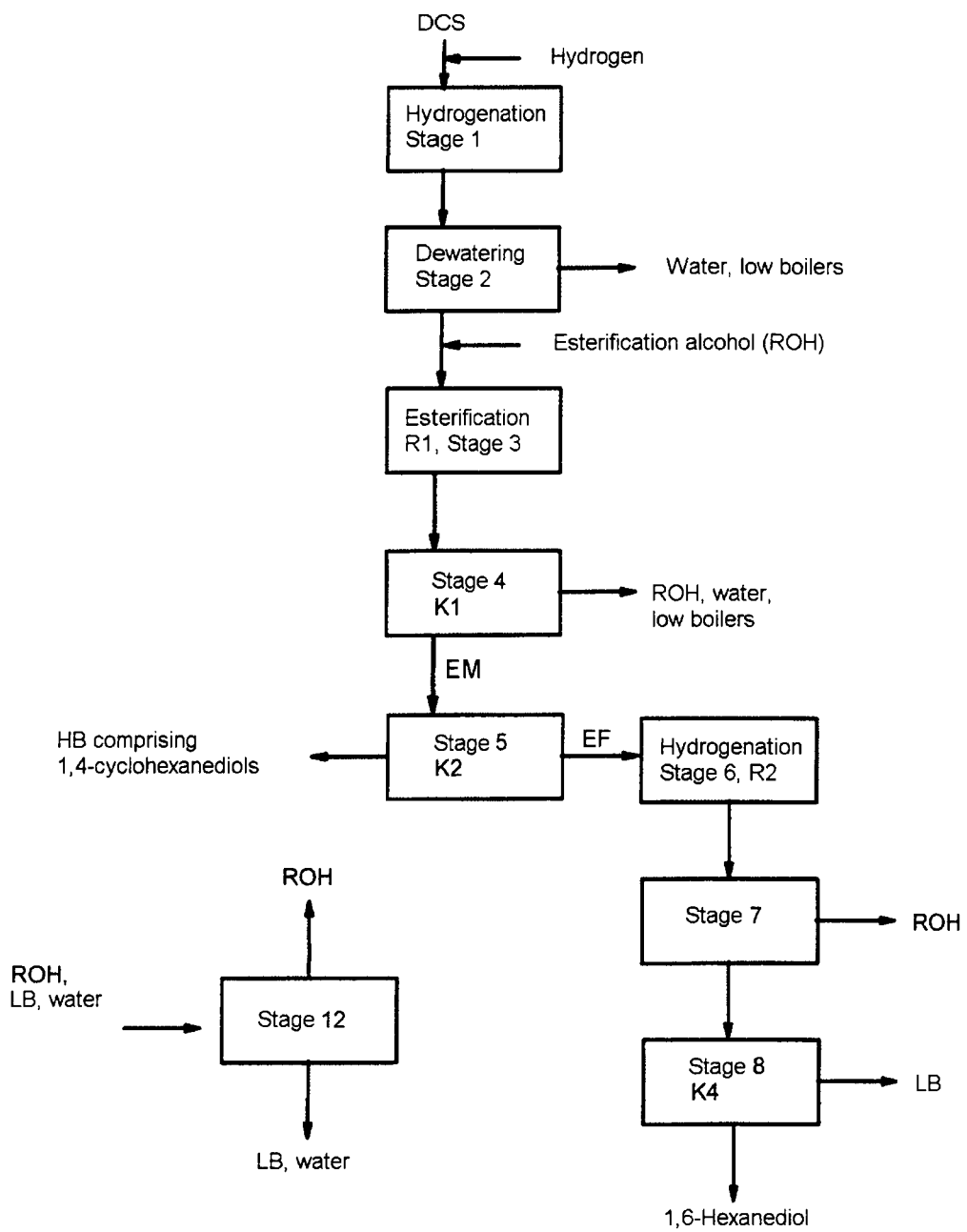

The invention relates to a process for preparing 1,6-hexanediol and caprolactone, preferably with at least 99.5% purity, which are especially virtually free of 1,4-cyclohexanediols, from a carboxylic acid mixture which is obtained as a by-product of the catalytic oxidation of cyclohexane to cyclohexanone/cyclohexanol with oxygen or oxygen-comprising gases and by water extraction of the reaction mixture, by hydrogenating the carboxylic acid mixture, esterifying and hydrogenating a substream to hexanediol and cyclizing 6-hydroxycaproic ester, the 1,4-cyclohexanediols being removed either in the course of fractionation of the esterification mixture or last from the caprolactone.

1,6-Hexanediol is a sought-after monomer unit which is used predominantly in the polyester and polyurethane sectors. Caprolactone or the polycaprolactones prepared therefrom from polyaddition serve to prepare polyurethanes.

The aqueous solutions of carboxylic acids which arise as by-products in the catalytic oxidation of cyclohexane to cyclohexanol and cyclohexanone (cf. Ullmann's Encyclopedia of Industrial Chemistry, 5th Ed., 1987, Vol. A8, p. 219), referred to hereinafter as dicarboxylic acid solution (DCS), comprise (calculated without water in % by weight) generally between 10 and 40% adipic acid, between 10 and 40% 6-hydroxycaproic acid, between 1 and 10% glutaric acid, between 1 and 10% 5-hydroxyvaleric acid, between 1 and 5% 1,2-cyclohexanediols, between 1 and 5% 1,4-cyclohexanediols, between 2 and 10% formic acid, between 0.5 and 5% 4-hydroxycyclohexanone, between 0.5 and 10% 6-oxocaproic acid and a multitude of further mono- and dicarboxylic acids, esters, oxo and oxa compounds, the individual contents of which generally do not exceed 5%. Examples include acetic acid, propionic acid, butyric acid, valeric acid, caproic acid, oxalic acid, malonic acid, succinic acid, 4-hydroxybutyric acid and 2- or 3-hydroxyadipic acid.

DE 2 321 101 and DE 1 235 879 disclose hydrogenating these aqueous dicarboxylic acid solutions at temperatures of 120 to 300° C. and pressures of 50 to 700 bar in the presence of predominantly cobalt-comprising catalysts to give 1,6-hexanediol as the main product. The hydrogenation outputs are preferably worked up by distillation. Even with an extremely high level of distillation complexity, it is possible to remove the 1,4-cyclohexanediols unchanged in the hydrogenation from 1,6-hexanediol only incompletely, if at all, such that the 1,4-cyclohexanediols which were already present initially in the DCS are found again in the 1,6-hexanediol with a content of generally 2 to 5% by weight.

In order to counter this problem, some approaches to solutions are known: U.S. Pat. No. 3,933,930 describes the conversion of 1,4-cyclohexandiol in aqueous solutions of adipic acid and 6-hydroxycaproic acid to cyclohexanol, cyclohexane and/or cyclohexene, by catalytically prehydrogenating the mixture. This process requires the use of two different hydrogenation catalysts, one for the prehydrogenation and one for the actual carboxylic acid hydrogenation, and is therefore costly and inconvenient.

According to DE-A 2 060 548, very pure 1,6-hexanediol is obtained by crystallization. This process too is very costly and inconvenient, and is also associated with considerable yield losses.

A further means of obtaining high-purity 1,6-hexanediol consists in hydrogenating, instead of DCS, pure adipic acid or pure adipic ester, as described by K. Weissermel, H. J. Arpe in Industrielle Organische Chemie [Industrial Organic Chemisry], VCH-Verlagsgemeinschaft Weinheim, 4th edition, page 263, 1994. However, pure adipic acid is very expensive compared to DCS. Furthermore, the carboxylic acid mixture obtained in the cyclohexane oxidation is a waste product which should be sent to a material utilization for environmental reasons among others. Caprolactone also cannot be obtained from adipic acid in a simple manner.

Caprolactone is prepared on the industrial scale predominantly on the basis of cyclohexanone by Baeyer-Villiger oxidation. Explosive percompounds are either used or passed through in the process.

The preparation of caprolactone from DCS has also already been described, for example, in DE 1 618 143. In this method, dewatered DCS is reacted thermally with phosphoric acid, and a mixture of dicarboxylic acids, caprolactone and a multitude of other components is fractionated. In some cases, the bottoms are obtained in solid and sparingly soluble form. However, even after further distillative workup, the caprolactone only has 98% purity.

Moreover, DE-A 2 013 525 and also EP-A 349861 describe conversion of 6-hydroxycaproic acid or esters thereof to caprolactone.

DE-A 196 07 954 already describes a process which describes obtaining 1,6-hexanediol and caprolactone from abovementioned aqueous carboxylic acid mixtures. This process, which is elegant in itself, however, still has certain disadvantages. For instance, not all linear C6 components present in the DCS are utilized for preparation of 1,6-hexanediol or caprolactone. For example, the 6-oxocaproic acid present is lost in the process and also reduces, as a result of high boiler formation, the distillation yields of intermediate esters needed for preparation of 1,6-hexanediol and optionally caprolactone. Moreover, the 1,6-hexanediol is not entirely free of undesired 1,4-cyclohexanediols, since they are removed efficiently as such in the process, but get into the hydrogenation as 4-hydroxycyclohexanone and give rise there to 1,4-cyclohexanediols in turn, which can be removed from 1,6-hexanediol only with difficulty. In addition, conversion products of 6-oxocaproic acid are detectable in the 1,6-hexanediol, for example 6,6-dimethoxyhexan-1-ol and 6-methoxyhexan-1-ol. These monoalcohols are generally very troublesome in polymer applications of diols, since they block one end in the course of chain formation. A further disadvantage is that the formic acid present in the DCS causes corrosion problems in the removal of water before the esterification stage, such that premium, expensive materials have to be used.

It was therefore an object of the present invention to provide a process for preparing 1,6-hexanediol and caprolactone, which enables, even proceeding from highly complex dicarboxylic acid solutions, the linear C6 carboxylic acids present therein to be converted as completely as possible to prepare very pure 1,6-hexanediol and very pure caprolactone, and hence the same or higher purity of the products to be achieved as known from the preparation process proceeding from pure adipic acid, without requiring additional and costly purification steps and/or materials.

This object is achieved by a process for preparing 1,6-hexanediol and ε-caprolactone from a carboxylic acid mixture which comprises adipic acid, 6-hydroxycaproic acid, 6-oxocaproic acid, 4-hydroxycyclohexanone, formic acid and, based on the sum of adipic acid and hydroxycaproic acid, between 0.5 and 5% by weight of 1,4-cyclohexanediols, and is obtained as a by-product of the catalytic oxidation of cyclohexane to cyclohexanone/cyclohexanol with oxygen or oxygen-comprising gases by water extraction of the reaction mixture, by esterifying and hydrogenating a substream to hexanediol and cyclizing 6-hydroxycaproic ester to caprolactone, which comprises a) hydrogenating only the aldehydes and ketones present in the aqueous carboxylic acid mixture catalytically to the corresponding alcohols and hydrogenating any C—C double bonds present to the corresponding saturated compounds and degrading more than 50% by weight of the formic acid present in the mixture,
b) reacting the mono- and dicarboxylic acids present in the aqueous reaction mixture, after dewatering, with a low molecular weight alcohol to give the corresponding carboxylic esters,
c) freeing the resulting esterification mixture of excess alcohol and low boilers in a first distillation stage,
d) in a second distillation stage, performing a separation of the bottom product into an ester fraction depleted of 1,4-cyclohexanediols and a fraction comprising 1,4-cyclohexanediols,
e) in a third distillation stage, at least partly removing a stream comprising predominantly 6-hydroxycaproic ester from the ester fraction,
f) catalytically hydrogenating the ester fraction from (e), from which 6-hydroxycaproic ester was removed at least partly, and obtaining 1,6-hexanediol in a manner known per se by distilling the hydrogenation product, and
g) heating the stream comprising predominantly 6-hydroxycaproic ester to temperatures greater than 200° C. under reduced pressure, which cyclizes 6-hydroxycaproic ester to caprolactone, and pure ε-caprolactone is obtained from the cyclization product by distillation.

The hydrogenation of a DCS is very complex since many compounds which can disrupt the actual hydrogenation or are likewise hydrogenated are present, which can complicate the subsequent workup. It was non-trivial and surprising that the hydrogenation of the aldehydes in step a) was so selective that the C6-hydroxycarboxylic acids present in the DCS were not already converted to 1,6-hexanediol in this step. Had this been the case, the 1,6-hexanediol formed would subsequently be removed together with the 1,4-cyclohexanediols in step d) of the process according to the invention, thus reducing the yield of 1,6-hexanediol. In addition, it was surprising that the catalyst used, in spite of the corrosive medium, has a high lifetime, and it was possible to lower the formation of high boilers in the process to such an extent that the yield of 1,6-hexanediol and caprolactone was improved significantly and that it was possible to crucially improve the purity of 1,6-hexanediol. Furthermore, it was not foreseeable that formic acid was degraded at least to an extent of 50%, and hence downstream stages are less affected by corrosion.

The esterification can be performed without addition of catalysts, but preferably under the action of catalysts. Useful low molecular weight alcohols are generally those having 1 to 10 carbon atoms, especially alkanols having 1 to 8 carbon atoms. Diols such as butanediol or pentanediol are also useful in principle. If caprolactone is to be obtained, the higher boiling alcohols than caprolactone are also useful, for example 1,6-hexanediol, octadecanol or trimethylolpropane.

The industrially preferred alcohols for use for the esterification are n- or i-butanol and especially methanol.

In the case of esterification with methanol, the procedure is to obtain, in the distillation stage (d), a methyl carboxylate fraction freed of 1,4-cyclohexanediols at the top of the column, and a bottom fraction comprising the high boilers and the 1,4-cyclohexanediols, and to catalytically hydrogenate the methyl carboxylate fraction in the hydrogenation stage (f).

In the process according to the invention, terms such as "via the top" or "via the bottom" each mean, respectively, removal above and below the feed of a distillation unit such as a column.

Figure 2:
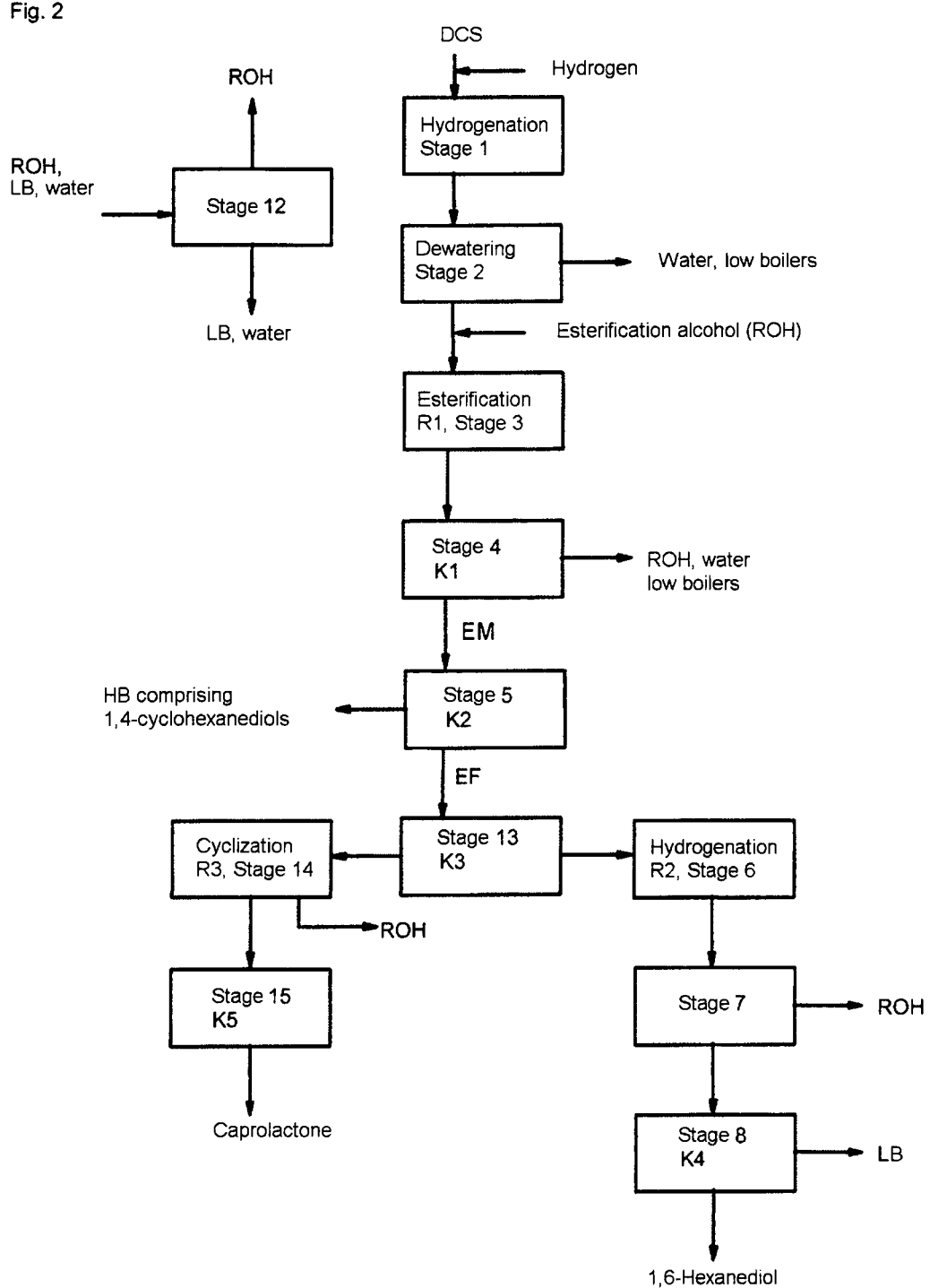

As shown in FIG. 1 and FIG. 2, the dicarboxylic acid solution (DCS) is hydrogenated, dewatered, then fed together with a $C_1$- to $C_3$-alcohol, preferably methanol, into the esterification reactor $R_1$ in which the carboxylic acids are esterified. The esterification mixture obtained then passes into the column $K_1$ in which the excess alcohol (ROH), water and low boilers (LB) are distilled off via the top, and the ester mixture (EM) is drawn off as bottoms and fed into column $K_2$. In this column, the EM is fractionated into an ester fraction (EF) which has been predominantly freed of 1,4-cyclohexanediols (a maximum of 5% by weight, preferably less than 1% by weight, of the 1,4-cyclohexanediols present in the feed) and a bottom fraction consisting of high boilers (HB) and cis- and trans-1,4-cyclohexanediols (1,4-CHDO). The ester fraction is then hydrogenated to 1,6-hexanediol and esterification alcohol, and purified by distillation in K4, or, if the intention is to obtain caprolactone, passed into a further fractionation column $K_3$ in which the ester fraction is separated into a top product comprising predominantly (>50% by weight) of adipic diester (ADE), preferably dimethyl adipate, and a bottom product comprising at least 90% by weight of 6-hydroxycaproic ester (HCE), preferably methyl 6-hydroxycaproate. The fraction comprising predominantly adipic diester is then hydrogenated in the catalytic hydrogenation $R_2$ to 1,6-hexanediol, which is purified by distillation in column $K_4$.

In reactor $R_3$, as described in FIG. 2, the 6-hydroxycaproic ester fraction is subjected to a thermal treatment at greater than 100° C., generally 150 to 350° C., preferably 200 to 300° C., under reduced pressure, for example 900 to 10 mbar, preferably 300 to 20 mbar; this leads to cyclization of the ester to form ε-caprolactone, which is purified by distillation in column $K_5$.

Figure 3:
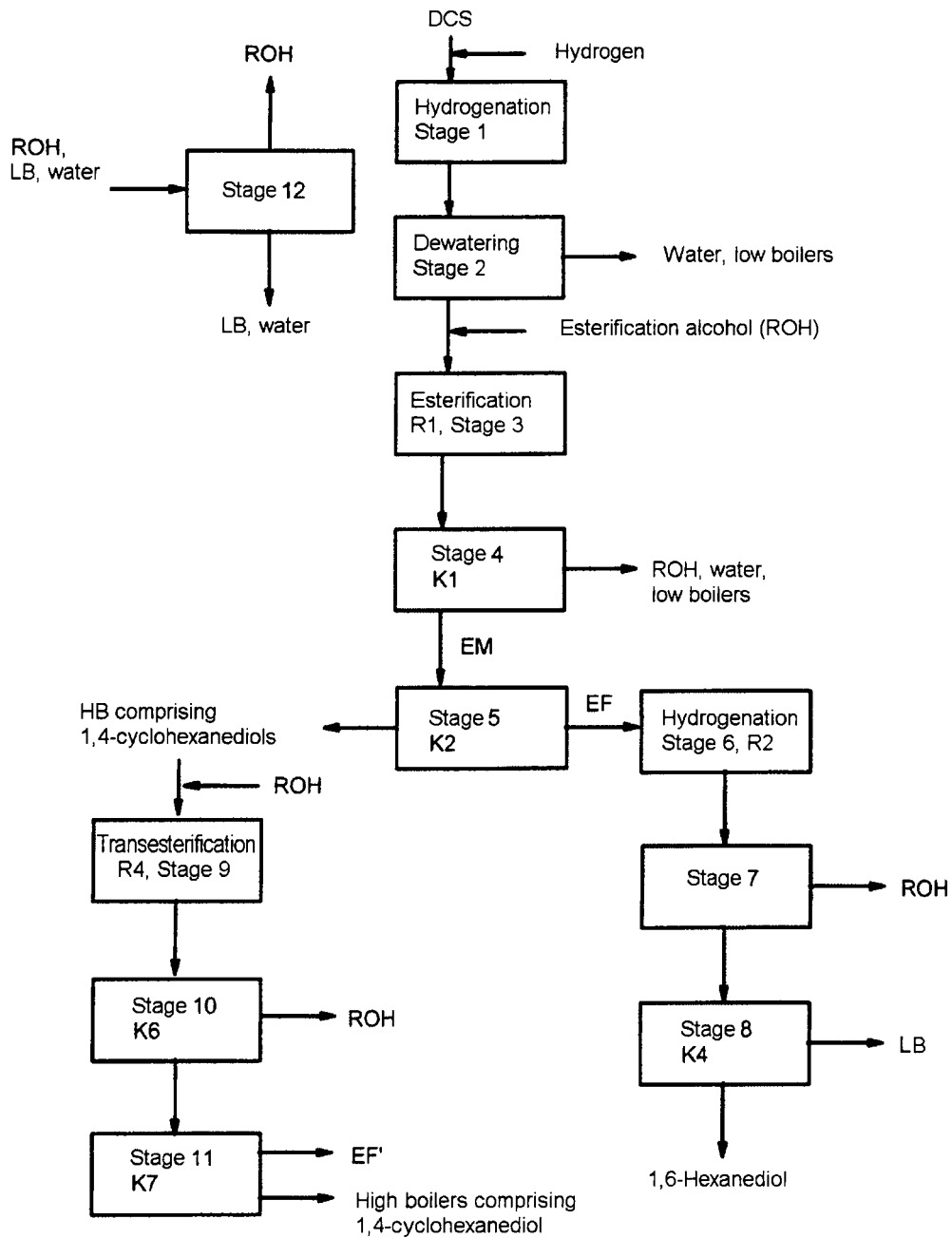

To enhance the overall yield of C6 products of value, as described in FIG. 3, the high boiler mixture obtained in column 2 can additionally be reacted once again with esterification alcohol ROH(R4), then freed of excess alcohol ROH in a further column $K_6$, and separated in a column K7 into high boilers which comprise the 1,4-cyclohexanediols and a further ester mixture EF'. This EF' can, for example, be fed back into column $K_2$ together with the ester mixture EM.

The process according to the invention is explained in detail hereinafter with reference to FIGS. 1 to 3.

The process steps are broken down into stages, stages 1, 2, 3, 4, 5, 6, 7 and 8, and 12, 13, 14 and 15, being essential to the process, and stages 4 and 5, and 7 and 8, also being combinable. Stages 9, 10 and 11 are optional, but may be advisable to increase the economic viability of the process.

For the catalytic hydrogenation of the DCS in step a) of the process according to the invention (stage 1), catalysts which comprise at least one metal of groups 7 to 12 of the periodic table, for example ruthenium, palladium, platinum, nickel, cobalt, iron, rhenium, iridium, copper, osmium and zinc, are used.

Preference is given to the metals ruthenium, nickel, cobalt, rhenium and copper. These metals can be used here in the form of the metals or of the compounds thereof, for example oxides and sulfides.

Preference is further given to mixtures or alloys of at least two of the metals of groups 7 to 12 of the periodic table. Examples include palladium/rhenium, platinum/rhenium and cobalt/copper.

Additionally very suitable are what are known as unsupported catalysts, which do not comprise a support and consist of metals, metal oxides or mixtures thereof. Preference is given to unsupported iron and especially cobalt catalysts.

The metals or metal compounds can be used without support. However, they are preferably applied to supports, for example $TiO_2$, $Al_2O_3$, $ZrO_2$, $SiO_2$, $HfO_2$, carbon, zeolites or mixtures thereof. These supported catalysts can be used in a wide variety of different finished forms, for example extrudates, tablets or rings.

Copper, nickel and cobalt can preferably be used in the form of Raney nickel, Raney copper or Raney cobalt. The Raney catalysts can also be used in all known finished forms, for example as tablets, extrudates or granules. Suitable Raney copper catalysts are, for example, Raney copper nuggets which are described in WO-A 99/03801.

Also particularly suitable for the hydrogenation of the DCS is a catalyst comprising ruthenium supported on shaped titanium dioxide bodies, the shaped titanium dioxide bodies being obtained by treating titanium dioxide, before or after shaping to the shaped body, with 0.1 to 30% by weight of an acid in which titanium dioxide is sparingly soluble.

The catalytically active ruthenium is applied by processes known per se, preferably to prefabricated $TiO_2$ as a support material.

A titanium dioxide support suitable with preference for use in the ruthenium-comprising catalyst can be obtained according to DE-A 197 38 464 by treating titanium dioxide, before or after the shaping of the shaped body, with 0.1 to 30% by weight of an acid, based on titanium dioxide, in which the titanium dioxide is sparingly soluble. Preference is given to using titanium dioxide in the anatase polymorph. Suitable acids of this kind are, for example, formic acid, phosphoric acid, nitric acid, acetic acid or stearic acid.

The active ruthenium component can be applied in the form of a ruthenium salt solution to the titanium dioxide support thus obtained in one or more impregnation stages. Subsequently, the impregnated support is dried and optionally calcined. It is, however, also possible to precipitate ruthenium out of a ruthenium salt solution, preferably with sodium carbonate, onto a titanium dioxide present in the form of powder in aqueous suspension. The precipitated solids are washed, dried, optionally calcined and shaped. In addition, volatile ruthenium compounds, for example ruthenium acetylacetonate or ruthenium carbonyl, can be converted to the gas phase and applied to the support in a manner known per se, which is referred to as chemical vapor deposition.

Other preferred support materials are zirconium oxide, silicon carbide and carbon. Especially carbon (activated carbons) has the advantage of low liter weight with simultaneously high surface area and chemical resistance to acids. The carbon supports can, before use, be pretreated oxidatively with, for example, air or nitric acid; likewise suitable is treatment with strong acids such as sulfuric acid, hydrochloric acid or phosphoric acid. The pretreatment generally leads to higher catalytic activity.

The supported catalysts thus obtained may be present in all known finished forms. Examples are extrudates, tablets or granules. Before they are used, the ruthenium catalyst precursors are reduced by treatment with hydrogenous gas, preferably at temperatures greater than 100° C. Before they are used in the process according to the invention, the catalysts are preferably passivated at temperatures of 0 to 50° C., preferably at room temperature, with oxygenous mixtures, preferably with air-nitrogen mixtures. It is also possible to install the catalyst into the hydrogenation reactor in oxidic form and to reduce it under reaction conditions.

The catalyst which is particularly preferred in accordance with the invention has a ruthenium content of 0.01 to 10% by weight, preferably of 0.1 to 6% by weight, based on the total weight of the catalyst composed of catalytically active metal and support. The inventive catalyst may have a sulfur content of 0.01 to 1% by weight, based on the total weight of the catalyst, the sulfur being determined by coulometric means.

The ruthenium surface area is from 1 to 20 $m^2$/g, preferably from 5 to 15 $m^2$/g, and the BET surface area (determined to DIN 66 131) from 5 to 500 $m^2$/g, preferably from 50 to 200 $m^2$/g.

The inventive catalysts have a pore volume of 0.1 to 100 ml/g. In addition, the catalysts feature a cutting hardness of 1 to 100 N.

The hydrogenation catalysts may be suspended in the reaction mixture. They are preferably arranged in fixed bed form in the hydrogenation reactor. The hydrogenation can be performed batchwise or preferably continuously. The reaction mixture can be passed over the catalyst in liquid phase mode or trickle mode.

The hydrogenation can be performed in a single reactor or in two series-connected reactors. When two reactors are used, the two reactors may comprise the same catalyst or two different catalysts. The two reactors may differ in the hydrogenation temperature and the partial hydrogen pressure.

It is additionally possible to perform the hydrogenation in a single reactor filled with a single catalyst, in such a way that the hydrogenation temperature in the reactor rises within a desired temperature range. The temperature range for the hydrogenation is between 50 and 200° C., preferably 70 to 180° C., more preferably between 90 and 160° C.

The reaction pressure, essentially generated by hydrogen, is between 1 and 100 bar absolute, preferably 3 to 50 bar, more preferably between 5 and 35 bar.

The hydrogen used may be pure hydrogen, but it is also possible, for industrial purposes even preferred, to completely or at least partly use the offgas from another hydrogenation, for example that of the esters to 1,6-hexanediol, for the hydrogenation.

The molar excess of hydrogen based on the component to be hydrogenated is between 1 and 5000 mol %, preferably 10 to 3000 mol %, more preferably 50 to 1000 mol %.

The dicarboxylic acid solution (DCS) is generally an aqueous solution with a water content of 20 to 80% by weight. Since an esterification reaction is an equilibrium reaction in which water forms, it is advisable, especially in the case of esterification with, for example, methanol, to remove water present before the reaction, in particular when water cannot be removed, for example azeotropically, during the esterification reaction. The dewatering (stage 2) in step b) can be effected, for example, with a membrane system, or preferably by means of a distillation apparatus in which water is removed via the top, and higher monocarboxylic acids, dicarboxylic acids and 1,4-cyclohexanediols via the bottom, at 10 to 250° C., preferably 20 to 200° C., more preferably 30 to 200° C., and a pressure of 1 to 1500 mbar, more preferably 5 to 1100 mbar, most preferably 20 to 1000 mbar. The bottom temperature is preferably selected such that the bottom product can be drawn off in liquid form. The water content in the bottom of the column may be 0.01 to 10% by weight, preferably 0.01 to 5% by weight, more preferably 0.01 to 1% by weight.

The water can be removed in such a way that the water is obtained in acid-free form, or the lower monocarboxylic acids present in the DCS—essentially formic acid if still present—can be distilled off for the most part with the water, preferably 60-95% by weight of the acids present in the feed, such as formic acid and acetic acid, in order that they do not bind any esterification alcohol in the esterification. Together with the water, it is also possible to remove further components, for example cyclohexanol, any cyclohexanone still present. These can be separated from water, for example, by phase separation and be released as products of value, for example, into the cyclohexanol/cyclohexanone recovery.

Alcohol ROH having 1 to 10 carbon atoms is added to the carboxylic acid stream from stage 2. It is possible to use methanol, ethanol, propanol or isopropanol, or mixtures of the alcohols, but preferably methanol on the one hand, or $C_4$ and higher alcohols, especially having 4 to 8 carbon atoms and preferably n- or i-butanol or else n-pentanol or i-pentanol on the other hand. The mixing ratio of alcohol to carboxylic acid stream (mass ratio) may be from 0.1 to 30, preferably 0.2 to 20, more preferably 0.5 to 10.

This mixture passes as a melt or solution into the reactor of stage 3, in which the carboxylic acids are esterified with the alcohol. The esterification reaction can be performed at 50 to 400° C., preferably 70 to 300° C., more preferably 90 to 200° C. It is possible to apply an external pressure, but preference is given to performing the esterification under autogenous pressure of the reaction system. The esterification apparatus used may be a stirred tank or flow tube, or it is possible to use a plurality of each. The residence time needed for the esterification is between 0.3 and 10 hours, preferably 0.5 to 5 hours. The esterification reaction can proceed without addition of a catalyst, but preference is given to adding a catalyst to increase the reaction rate. This may be a homogeneous dissolved catalyst or a solid catalyst. Examples of homogeneous catalysts include sulfuric acid, phosphoric acid, hydrochloric acid, sulfonic acids such as p-toluenesulfonic acid, heteropolyacids such as tungstophosphoric acid, or Lewis acids, for example aluminum, vanadium, titanium and boron compounds. Preference is given to mineral acids, especially sulfuric acid. The weight ratio of homogeneous catalyst to carboxylic acid melt is generally 0.0001 to 0.5, preferably 0.001 to 0.3.

Suitable solid catalysts are acidic or superacidic materials, for example acidic and superacidic metal oxides such as $SiO_2$, $Al_2O_3$, $SnO_2$, $ZrO_2$, sheet silicates or zeolites, all of which may be doped with mineral acids such as sulfate or phosphate for acid strengthening, or organic ion exchangers with sulfonic acid or carboxylic acid groups. The solid catalysts may be arranged as a fixed bed or be used as a suspension.

The water formed in the reaction is appropriately removed continuously, for example by means of a membrane or distillation.

The completeness of the conversion of the free carboxyl groups present in the carboxylic acid melt is determined with the acid number (mg KOH/g) measured after the reaction. Minus any acid added as a catalyst, it is 0.01 to 50, preferably 0.1 to 10. Not all carboxyl groups present in the system need be present as esters of the alcohols used, but a portion thereof may instead be present in the form of dimeric or oligomeric esters with the OH end of the hydroxycaproic acid.

The esterification mixture is fed into stage 4, a membrane system or preferably a distillation column. When a dissolved acid was used as the catalyst for the esterification reaction, the esterification mixture is appropriately neutralized with a base, in which case 1 to 1.5 base equivalents are added per acid equivalent of the catalyst. The bases used are generally alkali metal or alkaline earth metal oxides, carbonates, hydroxides or alkoxides, or amines in substance or dissolved in the esterification alcohol. It is likewise possible to use ion exchangers, which are preferably reusable time and again by regeneration.

When a column is used in stage 4, the feed to the column is preferably between the top stream and the bottom stream. The excess esterification alcohol ROH, water and corresponding esters of formic acid, acetic acid and propionic acid are drawn off via the top at pressures of 1 to 1500 mbar, preferably 20 to 1000 mbar, more preferably 40 to 800 mbar, and temperatures between 0 and 150° C., preferably 15 and 90° C. and especially 25 and 75° C. This stream can either be combusted or preferably worked up further in stage 12.

The bottoms obtained are an ester mixture which consists predominantly of the esters of the alcohol ROH used with dicarboxylic acids such as adipic acid and glutaric acid, hydroxycarboxylic acids such as 6-hydroxycaproic acid and 5-hydroxyvaleric acid, and of oligomers and free or esterified 1,4-cyclohexanediols. It may be advisable to permit a residual content of water and/or alcohol ROH up to 4% by weight each in the ester mixture. The bottom temperatures are 70 to 250° C., preferably 80 to 220° C., more preferably 100 to 190° C.

The stream from stage 4, which has been substantially freed of water and esterification alcohol ROH, is fed into stage 5. This is a distillation column in which the feed is between the low-boiling components and the high-boiling components. The column is operated at temperatures of 10 to 300° C., preferably 20 to 270° C., more preferably 30 to 250° C., and pressures of 1 to 1000 mbar, preferably 5 to 500 mbar, more preferably 10 to 200 mbar.

The top fraction consists predominantly of residual water and residual alcohol ROH, esters of the alcohol ROH with monocarboxylic acids, predominantly $C_3$- to $C_6$-monocarboxylic esters with hydroxycarboxylic acids such as 6-hydroxycaproic acid, 5-hydroxyvaleric acid, and in particular the diesters with dicarboxylic acids such as adipic acid, glutaric acid and succinic acid, and 1,2-cyclohexanediols, caprolactone and valerolactone.

The components mentioned may be removed together via the top or, in a further preferred embodiment, be separated in the column of stage 5 into a top stream comprising predominantly residual water and residual alcohol and the abovementioned constituents having 3 to 5 carbon atoms, and a sidestream comprising predominantly the abovementioned constituents of the $C_6$ esters. The stream comprising the esters of the $C_6$ acids, either as an overall top stream or as a sidestream, can then, according to how much caprolactone is to be prepared, in the limiting case—without caprolactone preparation—pass entirely into the hydrogenation (stage 6), but is fed in accordance with the invention partly or as the entire stream into stage 13.

The high-boiling components of the stream from stage 4, predominantly consisting of 1,4-cyclohexanediols or esters thereof, dimeric or oligomeric esters and constituents of the DSC, some of them polymeric, which are not defined in detail, are removed via the stripping section of the column of stage 5. These may be obtained together or in such a way that predominantly the 1,4-cyclohexanediols are removed via a sidestream of the column in the stripping section and the rest via the bottom. The 1,4-cyclohexanediols thus obtained may find use, for example, as a starting material for active ingredients. The high-boiling components, with or without the 1,4-cyclodiol content, can either be incinerated or, in a preferred embodiment, passed to the so-called transesterification in stage 9.

Stages 4 and 5 can, especially when only relatively small amounts are processed, be combined. To this end, for example, the $C_6$ ester stream can be obtained in a fractional distillation performed batchwise, again without 1,4-cyclohexanediols getting into the stream conducted to the hydrogenation.

The hydrogenation is effected catalytically either in the gas or liquid phase. Useful catalysts in principle include all homogeneous and heterogeneous catalysts suitable for hydrogenation of carbonyl groups, such as metals, metal oxides, metal compounds or mixtures thereof. Examples of homogeneous catalysts are described in H. Kropf, Houben-Weyl, Methoden der Organischen Chemie [Methods of Organic Chemistry], volume IV/1c, Georg Thieme Verlag Stuttgart, 1980, p. 45 to 67, and examples of heterogeneous catalysts are described in Houben-Weyl, Methoden der Organischen Chemie, volume IV/1c, p. 16 to 26.

Preference is given to using catalysts which comprise one or more of the elements from transition groups I and VI to VIII of the periodic table of the elements, preferably copper, chromium, molybdenum, manganese, rhenium, ruthenium, cobalt, nickel and palladium, more preferably copper, cobalt or rhenium.

The catalysts may consist solely of the active components, or the active components may be applied to supports. Suitable support materials are, for example, $Cr_2O_3$, $Al_2O_3$, $SiO_2$, $ZrO_2$, $TiO_2$, $ZnO_2$, $BaO$ or $MgO$ or mixtures thereof.

Particular preference is given to catalysts as described in EP 0 552 463. These are catalysts which possess, in the oxidic form, the composition

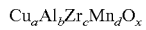

$Cu_aAl_bZr_cMn_dO_x$ where a>0, b>0, c≙0, d>0, a>b/2, b>a/4, a>c, a>d, and x denotes the number of oxygen ions required per formula unit to provide electrical neutrality. These catalysts can be prepared, for example, according to specifications of EP 0 552 463 by precipitation of sparingly soluble compounds from solutions which comprise the corresponding metal ions in the form of salts thereof. Suitable salts are, for example, halides, sulfates and nitrates. Suitable precipitants are all agents which lead to the formation of such insoluble intermediates, which can be converted to the oxides by thermal treatment. Particularly suitable intermediates are the hydroxides and carbonates or hydrogencarbonates, and so the particularly preferred precipitants used are alkali metal carbonates or ammonium carbonate. An important feature for the preparation of the catalysts is the thermal treatment of the intermediates at temperatures between 500° C. and 1000° C. The BET surface area of the catalysts is between 10 and 150 m$^2$/g.

Further preferred hydrogenation catalysts comprise, as well as Cu, also lanthanum and aluminum oxides. They are described, for example, in DE-A 10313702.

Preference is given to using heterogeneous catalysts which are either arranged in fixed bed form or used as a suspension. When the hydrogenation is performed in the gas phase and over catalyst arranged in fixed bed form, temperatures of 150 to 300° C. are generally employed at pressures of 1 to 100 bar, preferably 15 to 70 bar. Appropriately, at least a sufficient amount of hydrogen as a hydrogenating agent and carrier gas is used that reactants, intermediates and products never become liquid during the reaction. The excess hydrogen is preferably circulated, in which case a small portion can be discharged as offgas to remove inerts, for example methane. It is possible to use one reactor or a plurality of reactors connected in series.

When the hydrogenation is effected in the liquid phase with fixed bed or suspended catalyst, it is generally performed at temperatures between 100 and 350° C., preferably 120 and 300° C., and pressures of 30 to 350 bar, preferably 40 to 300 bar.

The hydrogenation can be performed in one reactor or a plurality of reactors connected in series. The hydrogenation in the liquid phase over a fixed bed can be performed either in trickle mode or liquid phase mode. In a preferred embodiment, a plurality of reactors are used, in which case the predominant portion of the esters is hydrogenated in the first reactor and the first reactor is preferably operated with liquid circulation for heat removal and the downstream reactor(s) is/are preferably operated without circulation to complete the conversion. Cycle gas is unnecessary especially in trickle mode.

The hydrogenation can be performed batchwise, preferably continuously.

The hydrogenation output consists essentially of 1,6-hexanediol and the alcohol ROH. Further constituents are in particular, if the overall low-boiling stream of stage 5 was used, 1,5-pentanediol, 1,4-butanediol, 1,2-cyclohexanediols and small amounts of monoalcohols having 1 to 6 carbon atoms, optionally ethers and water.

The hydrogenation output is separated in stage 7, for example a membrane system or preferably a distillation column, into the alcohol ROH which additionally comprises the majority of the further low-boiling components and a stream which comprises predominantly 1,6-hexanediol in addition to 1,5-pentanediol and the 1,2-cyclohexanediols. Top temperatures of 0 to 120° C., preferably 20 to 100° C., more preferably 30 to 90° C., and bottom temperatures of 100 to 270° C., preferably 140 to 260° C., more preferably 160 to 250° C., are established at a pressure of 10 to 1500 mbar, preferably 30 to 1200 mbar, more preferably 50 to 1000 mbar. The low-boiling stream can either be returned directly into the esterification of stage 3 or pass into stage 9 or into stage 12.

The stream comprising 1,6-hexanediol is purified in a column in stage 8. In this purification, 1,5-pentanediol, the 1,2-cyclohexanediols and any further low boilers present are removed via the top. If the 1,2-cyclohexanediols and/or 1,5-pentanediol are to be obtained as additional products of value, they can be separated in a further column. Any high boilers present are discharged via the bottom. 1,6-Hexanediol with a purity of at least 99.5%, preferably at least 99.7%, more preferably more than 99.9%, is withdrawn from a sidestream of the column. Top temperatures of 50 to 200° C., preferably 60 to 150° C., and bottom temperatures of 130 to 270° C., preferably 150 to 250° C., are established at pressures of 1 to 1000 mbar, preferably 5 to 800 mbar, more preferably 20 to 500 mbar.

If only small amounts of 1,6-hexanediol are to be prepared, stages 7 and 8 can also be combined in a batchwise fractional distillation.

In order to operate the process according to the invention in a very economically viable manner, it is advisable to recover the esterification alcohol ROH and to use it time and again for the esterification. To this end, the stream comprising predominantly the alcohol ROH from stage 4 and/or 7 can be worked up in stage 12. To this end, it is advantageous to use a column in which lower-boiling components than the alcohol ROH are removed via the top, and water and higher-boiling components than the alcohol ROH are removed via the bottom, from the alcohol ROH which is obtained in a sidestream. The column is appropriately operated at 500 to 5000 mbar, preferably at 800 to 3000 mbar.

In a further preferred embodiment of the process according to the invention, the high-boiling stream from stage 5 is worked up to increase the overall yield of products of value, based on the DCS used. To this end, in stage 9, the proportion of dimeric and oligomeric esters of adipic acid or hydroxycaproic acid is reacted with further amounts of the alcohol ROH, preferably methanol, in the present of a catalyst. The weight ratio of alcohol ROH and the bottom stream from stage 5 is between 0.1 and 20, preferably 0.5 to 10, more preferably 1 to 5. Suitable catalysts are in principle those already described for the esterification in stage 3. Preference is given, however, to using Lewis acids or Lewis bases. Examples thereof are compounds or complexes of aluminum, tin, antimony, zirconium or titanium, such as zirconium acetylacetonate or tetraalkyl titanate such as tetraisopropyl titanate, which are employed in concentrations of 1 to 10 000 ppm, preferably 50 to 6000 ppm, more preferably 100 to 4000 ppm. Particular preference is given to titanium compounds.

The transesterification can be performed batchwise or continuously, in one reactor or a plurality of reactors, in series-connected stirred tanks or tubular reactors, at temperatures between 100 and 300° C., preferably 120 to 270° C., more preferably 140 to 240° C., and the autogenous pressures which are established. The residence times required are 0.5 to 10 hours, preferably 1 to 4 hours.

In the case of esterification with methanol, this stream from stage 9 can be fed, for example, back into stage 4. To prevent accumulations, in particular of 1,4-cyclohexanediols, a substream of the high boilers from stage 5 must then be discharged batchwise or continuously. Another option is to recycle the stream from stage 9 not into stage 4, but to separate it, analogously to stage 4, in a stage 10 into predominantly alcohol ROH, which can then pass back into stage 3, 9 or 12, and a stream which comprises the esters.

This ester stream can in principle (with the proviso of preventing accumulations of the 1,4-cyclohexanediols) be recycled into stage 5, or is preferably separated in a further stage 11 into the esters of the $C_6$ acids and, in a relatively insignificant amount, into the esters of the $C_5$ acids on the one hand, which are either fed into stage 5 or directly into stage 6, and high boilers on the other hand, which comprise 1,4-cyclohexanediols, and then the high boilers are discharged.

For the caprolactone preparation, the stream comprising predominantly esters of the $C_6$ acids from stage 5 is used. To this end, this stream is separated in stage 13, a distillation column, into a stream which comprises predominantly adipic diesters and comprises the 1,2-cyclohexanediols present via the top, and a stream which comprises predominantly 6-hydroxycaproic ester and does not comprise any 1,2-cyclohexanediols via the bottom. The column is operated at pressures of 1 to 500 mbar, preferably 5 to 350 mbar, more preferably 10 to 200 mbar, and bottom temperatures of 80 to 250° C., preferably 100 to 200° C., more preferably 110 to 180° C. The top temperatures are established correspondingly.

An important feature for a high purity and high yield of caprolactone is the removal of the 1,2-cyclohexanediols from the hydroxycaproic ester, since these components form azeotropes with one another.

To reduce the separation complexity, it may be advantageous also to remove some hydroxycaproic ester in stage 13 together with the adipic diester. The hydroxycaproic ester content is advantageously between 0.2 and 15% by weight. According to the alcohol component of the esters, this proportion of hydroxycaproic ester is removed together with the adipic diester via the top (e.g. methyl ester) or via the bottom (e.g. butyl ester).

The bottom stream comprising 6-hydroxycaproic ester from stage 13 is converted in stage 14 in a manner known per se, either in the gas or liquid phase, to alcohol and caprolactone. Preference is given to the liquid phase.

The reaction is performed without catalyst or else preferably in the presence of a catalyst. Suitable catalysts are acidic or basic catalysts which may be present in homogeneously dissolved or heterogeneous form. Examples are alkali metal and alkaline earth metal hydroxides, oxides, carbonates, alkoxides or carboxylates, acids such as sulfuric acid or phosphoric acid, organic acids such as sulfonic acids or mono- or dicarboxylic acids, or salts of the aforementioned acids, Lewis acids or Lewis bases, preferably from main groups III and IV or transition groups I to VIII of the periodic table of the elements.

Preference is given to using the same catalysts which are also used in stage 9, since the high-boiling discharge stream of stage 14 comprises oligomeric hydroxycaproic acid units, which can advantageously be reutilized via stage 9. When a heterogeneous catalyst is used, the catalyst hourly space velocity is typically 0.05 to 5 kg of reactant/l of catalyst and hour. In the case of homogeneous catalysts, the catalyst is preferably added to the reactant stream. The concentration is typically 10 to 10 000 ppm, preferably 50 to 5000 ppm, more preferably 100 to 1000 ppm. The reaction is typically performed at 150 to 400° C., preferably 180 to 350° C., more preferably 190 to 280° C., and pressures of 1 to 1020 mbar, preferably 5 to 500 mbar, more preferably 10 to 200 mbar.

In some cases, it is advantageous to perform the cyclization reaction in the presence of high-boiling mono-, di- or polyols, for example decanol, undecanol, tridecanol, pentadecanol, octadecanol, 1,4-butanediol, 1,5-pentanediol, 1,6-hexanediol, 1,4-cyclohexanediols, butylethylpropanediol, neopentyl glycol, triethylene glycol, tetraethylene glycol, trimethylolpropane or glycerol.

These high-boiling alcohols or polyols are initially charged and/or added to the reaction mixture in concentrations up to 5% by weight or metered in separately, for example in each case in concentrations of 1 to 20 000 ppm, preferably 10 to 4000 ppm, more preferably 50 to 2000 ppm.

When the cyclization is performed in the liquid phase, the reaction products, predominantly esterification alcohol ROH and caprolactone, are removed from the reaction mixture in gaseous form. A column attached to the reaction vessel is advantageous, in which as yet unconverted reactant can be retained within the reaction system, and the alcohol and caprolactone are drawn off via the top. The product stream can be condensed in such a way that fractional condensation is effected, i.e. first predominantly caprolactone, then the esterification alcohol. It will be appreciated that it is also possible to obtain only the alcohol via the top, but caprolactone in a sidestream. The alcohol stream can advantageously be recycled into stage 3, 9 or 12. The bottom product of the cyclization can be fed into stage 9.

The feed to the reaction vessel may not be preheated. When homogeneous catalysts are used, it is advantageous to introduce the reactant stream directly into the cyclization bottoms. The catalyst in this case may either be added to the feed actually before the reaction, or be added directly to the reaction vessel.

However, it is more advantageous to preheat the feed, in particular when the catalyst is already dissolved and a hydroxycaproic ester with a $C_1$-$C_5$-alcohol component is used. The preheating temperature is between 100 and 300° C., preferably 130-270° C., more preferably 150-250° C. At these temperatures, the hydroxycaproic ester already reacts partly to give the alcohol, caprolactone and dimeric or oligomeric hydroxycaproic esters. This has the effect that only a little hydroxycaproic ester, when it gets into the hot reaction vessel, can distill immediately out of the reaction bottoms. In this way, column trays can be saved.

A further advantageous option consists in obtaining the predominant portion of the ester alcohol before the workup of the caprolactone, in particular when this alcohol, such as methanol, is low-boiling and as a consequence would be condensable only with difficulty. To this end, the methyl hydroxycaproate is preheated in the presence of a catalyst as described above, in the course of which the alcohol released is already distilled off. This is advantageously done at 100-

1100 mbar, a pressure range in which the ester alcohol is readily condensable. This procedure is also possible in the presence of the above-described high-boiling alcohols.

The caprolactone product stream of stage 14 is worked up further in stage 15. This may comprise one or more columns. When one column is used, any esterification alcohol still present and other $C_1$ to $C_6$ low boilers are removed via the top, pure caprolactone is removed via a sidestream and any as yet unconverted hydroxycaproic ester is removed via the bottom and recycled.

High-purity caprolactone is obtained when, in stage 15, the low boilers mentioned are drawn off in a first column via the top, and caprolactone and other high boilers via the bottom, are fed into a second column where caprolactone is drawn off via the top. When the caprolactone stream to be obtained is only in relatively small amounts, caprolactone can be obtained with one column by batchwise fractional distillation.

The distillations are performed at bottom temperatures of 70 to 250° C., preferably 90 to 230° C., more preferably 100 to 210° C., and pressures of 1 to 500 mbar, preferably 5 to 200 mbar, more preferably 10 to 150 mbar.

In the process according to the invention, yields of 1,6-hexanediol and caprolactone each of more than 95% can be achieved with purities of more than 99%.

The process is illustrated in detail with reference to the examples which follow, but is not restricted in any way as a result. The figures regarding the composition of the streams are % by weight determined by gas chromatography.

EXAMPLE 1

Comparative Example without Hydrogenation of the DCS

Stage 2: (Dewatering)

0.1 kg of dicarboxylic acid solution/h (adipic acid, 6-hydroxycaproic acid, 6-oxocaproic acid, 1,4-cyclohexanediols, 4-hydroxycyclohexanone, glutaric acid, 5-hydroxyvaleric acid, formic acid, water) was distilled continuously in a distillation apparatus (three-tray bubble-cap tray column with external oil heating circuit, oil temperature 150° C., tray volume approx. 25 ml each, feed via the bubble-cap trays) with an attached column with random packing (approx. 4 theoretical plates, no return stream at the top). The top product obtained was 0.045 kg with a formic acid content in water of approx. 3%. The water content in the bottom stream (5.5 kg) was approx. 0.4%.

Stage 3: (Esterification)

5.5 kg of the bottom stream from stage 1 were reacted with 8.3 kg of methanol and 14 g of sulfuric acid. The acid number of the output minus sulfuric acid was approx. 10 mg KOH/g.

Stage 4:

In a column, the esterification stream from stage 2 was distilled (1015 mbar, top temperature 65° C., bottom temperature up to 125° C.). 7.0 kg were drawn off via the top. The bottom product obtained was 6.8 kg.

Stage 5: (1,4-Cyclohexanediol Removal)

In a 50 cm column with random packing, the bottom stream from stage 3 was fractionally distilled (10 mbar, top temperature 75-90° C., bottom temperature up to 200° C.). The 1,4-cyclohexanediols were found in the bottoms.

The low boilers distilled off were 0.3 kg (dimethyl succinate, methyl valerate, methyl pentanoate, methyl caproate, 1,2-cyclohexanediols, valerolactone, methyl 5-hydroxyvalerate, dimethyl glutarate, among others); as the fraction comprising predominantly dimethyl adipate and methyl 6-hydroxycaproate, 4.6 kg were obtained, which also comprised between 2 and 5% dimethyl glutarate and methyl 5-hydroxyvalerate, between 0.2 and 1% valerolactone, caprolactone, methyl 6,6-dimethoxycaproate and 4-hydroxycyclohexanone.

Stage 6: (Substream Hydrogenation)

2.7 kg of $C_6$ ester mixture from stage 5 were hydrogenated continuously over a catalyst in a 25 ml reactor (catalyst: 70% by weight of CuO, 25% by weight of ZnO, 5% by weight of $Al_2O_3$, which has been activated beforehand in a hydrogen stream at 180° C., hydrogenation conditions: feed 20 g/h, no circulation, 220 bar, 220° C.). The ester conversion was 99.5%; the 1,6-hexanediol selectivity was more than 99%.

Stages 7 and 8: (Hexanediol Purification)

2.5 kg of the hydrogenation output from stage 6 were fractionally distilled (distillation still with attached 70 cm column with random packing, reflux ratio 2). At 1013 mbar, 0.5 kg of methanol was distilled off and, after applying vacuum (20 mbar), predominantly the 1,2-cyclohexanediols and 1,5-pentanediol distilled off. Thereafter (b.p. 146° C.), 1,6-hexanediol distilled off with a purity of 99.6%. In addition to quantitatively insignificantly components, approx. 0.2% 1,4-cyclohexanediols and approx. 0.02% 6-methoxyhexan-1-ol and 0.1% 6,6-dimethoxyhexan-1-ol were found in the hexanediol.

Stage 13: (Adipic Ester Separation from 6-hydroxycaproic Ester)

In a 3 l distillation still with attached column (50 cm, 5 mm V2A metal ring random packings) and reflux divider, predominantly dimethyl adipate was distilled off at 10 mbar from 2.0 kg of ester mixture from stage 4 (reflux ratio 5, top temperature up to 100° C., bottom temperature up to 120° C.). In the bottoms, 0.5 kg of methyl hydroxycaproate remained (82%, remainder predominantly dimeric methyl hydroxycaproate, no dimethyl adipate).

Stage 14: (Cyclization)

A 250 ml distillation still with external heating and attached column (70 cm, 5 mm V2A metal ring random packings) with a reflux divider was initially charged with 10 g of 1,6-hexanediol with addition of 3000 ppm of tetraisopropyl titanate, which were heated to 200° C. at 40 mbar, and 35 ml/h of bottom product from stage 13, to which 1000 ppm of tetraisopropyl titanate and 200 ppm of 1,6-hexanediol had been added, were fed in. At a top temperature of 123 to 124° C. and a reflux ratio of 4, predominantly caprolactone condensed at 25° C., and methanol at −78° C.

Stage 15: (Caprolactone Purification)

In a 250 ml distillation still with attached column (70 cm, 5 mm V2A metal ring random packings) and reflux divider (reflux ratio 4), the caprolactone obtained from stage 13 was fractionally distilled at 40 mbar. After removing essentially valerolactone (b.p. 90 to 110° C.), caprolactone (b.p. 131° C.) was obtained in a purity (GC area %) of 99.9%.

EXAMPLE 2

Inventive Example

Stage 1: (DCS Hydrogenation)

0.1 kg/h of dicarboxylic acid solution was hydrogenated in a tubular reactor (length 1 m, capacity 100 ml) at 120° C. and hydrogen pressure 20 bar, 25 standard liters of hydrogen/h over 100 ml of an Ru (5%)/titanium dioxide catalyst. The hydrogenation was conducted for 500 h without the composition of the hydrogenation output changing significantly. The 1,6-hexanediol content after the hydrogenation was less than 0.1% higher than before the hydrogenation.

Stage 2: (Dewatering)

0.1 kg/h of dicarboxylic acid solution from stage 1 (adipic acid, 6-hydroxycaproic acid, 1,4-cyclohexanediols, glutaric acid, 5-hydroxyvaleric acid, formic acid, water) was distilled continuously in a distillation apparatus (three-tray bubble-cap tray column with external oil heating circuit, oil temperature 150° C., tray volume approx. 25 ml each, feed via the bubble-cap tray) with an attached column with random packing (approx. 4 theoretical plates, no return stream at the top). The top product obtained was 0.04 kg with a formic acid content in water of approx. 0.2%. In the bottom stream (5.5 kg), the water content was approx. 0.4%.

The comparison between the comparative example and the inventive example shows a significantly smaller amount of formic acid, as a result of which a purer end product (see stage 7/8) than known in the prior art is obtained.

Stage 3: (Esterification)

5.5 kg of the bottom stream from stage 1 were reacted with 8.3 kg of methanol and 14 g of sulfuric acid. The acid number of the output minus sulfuric acid was approx. 10 mg KOH/g.

Stage 4:

In a column, the esterification stream from stage 2 was distilled (1015 mbar, top temperature 65° C., bottom temperature up to 125° C.). 7.0 kg were drawn off via the top. The bottom product obtained was 6.8 kg.

Stage 5: (1,4-Cyclohexanediol Removal)

In a 50 cm column with random packing, the bottom stream from stage 3 was fractionally distilled (10 mbar, top temperature 75-90° C., bottom temperature up to 200° C.). The 1,4-cyclohexanediols were found in the bottoms.

The low boilers distilled off were 0.3 kg (dimethyl succinate, methyl valerate, methyl pentanoate, methyl caproate, 1,2-cyclohexanediols, valerolactone, methyl 5-hydroxyvalerate, dimethyl glutarate, among others); as the fraction comprising predominantly dimethyl adipate and methyl 6-hydroxycaproate, 5.5 kg were obtained, which also comprised between 2 and 5% dimethyl glutarate and methyl 5-hydroxyvalerate, between 0.2 and 1% valerolactone and caprolactone.

Stage 6: (Substream Hydrogenation)

3 kg of $C_6$ ester mixture from stage 5 were hydrogenated continuously over a catalyst in a 25 ml reactor (catalyst: 70% by weight of CuO, 25% by weight of ZnO, 5% by weight of $Al_2O_3$, which has been activated beforehand in a hydrogen stream at 180° C., hydrogenation conditions: feed 20 g/h, no circulation, 220 bar, 220° C.). The ester conversion was 99.5%; the 1,6-hexanediol selectivity was more than 99%.

Stages 7 and 8: (Hexanediol Purification)

2.9 kg of the hydrogenation output from stage 6 were fractionally distilled (distillation still with attached 70 cm column with random packing, reflux ratio 2). At 1013 mbar, 0.6 kg of methanol was distilled off and, after applying vacuum (20 mbar), predominantly the 1,2-cyclohexanediols and 1,5-pentanediol distilled off. Thereafter (b.p. 146° C.), 1,6-hexanediol distilled off with a purity of 99.93%. In the hexanediol, in addition to quantitatively insignificant components, only approx. 0.01% 1,4-cyclohexanediols was found. 6-Methoxyhexan-1-ol and 6,6-dimethoxyhexan-1-ol were not found.

Stage 13: (Adipic Ester Separation from 6-hydroxycaproic Ester)

In a 3 l distillation still with attached column (50 cm, 5 mm V2A metal ring random packings) and reflux divider, predominantly dimethyl adipate was distilled off at 10 mbar from 2.5 kg of ester mixture from stage 4 (reflux ratio 5, top temperature up to 100° C., bottom temperature up to 120° C.).

In the bottoms, 0.5 kg of methyl hydroxycaproate remained (82%, remainder predominantly dimeric methyl hydroxycaproate, no dimethyl adipate).

Stage 14: (Cyclization)

A 250 ml distillation still with external heating and attached column (70 cm, 5 mm V2A metal ring random packings) with a reflux divider was initially charged with 10 g of 1,6-hexanediol with addition of 3000 ppm of tetraisopropyl titanate, which were heated to 200° C. at 40 mbar, and 35 ml/h of bottom product from stage 13, to which 1000 ppm of tetraisopropyl titanate and 200 ppm of 1,6-hexanediol had been added, were fed in. At a top temperature of 123 to 124° C. and a reflux ratio of 4, predominantly caprolactone condensed at 25° C., and methanol at −78° C.

Stage 15: (Caprolactone Purification)

In a 250 ml distillation still with attached column (70 cm, 5 mm V2A metal ring random packings) and reflux divider (reflux ratio 4), the caprolactone obtained from stage 13 was fractionally distilled at 40 mbar. After removing essentially valerolactone (b.p. 90 to 110° C.), caprolactone (b.p. 131° C.) was obtained in a purity (GC area %) of 99.9%.

EXAMPLE 3

Example 2 stage 1 was repeated, with the difference that the catalyst used was Ru (0.5%) on activated carbon. The hydrogenation result was equivalent to example 2.

EXAMPLE 4

Example 2 stage 1 was repeated, with the difference that the catalyst used was Ni (10%) on activated carbon at 150° C. and 50 bar. The hydrogenation result was equivalent to example 2.

EXAMPLE 5

Example 2 stage 1 was repeated, with the difference that the catalyst used was Co (10%) on activated carbon at 120° C. and 50 bar. The hydrogenation result was equivalent to example 2.

The invention claimed is:

1. A process for preparing 1,6-hexanediol and ε-caprolactone from a carboxylic acid mixture, the process comprising:
 a) hydrogenating, in a first hydrogenation, employing a catalyst, only any aldehyde or ketone present in the carboxylic acid mixture to a corresponding alcohol and degrading more than 50% of formic acid present in the carboxylic acid mixture, to obtain a first hydrogenation mixture, wherein the catalyst for the first hydrogenation comprises at least one metal selected from the group consisting of Ru, Re, Co, Ni, and Cu, and the hydrogenating is carried out at a temperature of from 50 to 200° C. and at a pressure of from 5 to 35 bar;
 b) dewatering the first hydrogenation mixture to obtain a dewatered hydrogenation mixture;
 c) reacting, in a first esterification, any mono- or dicarboxylic acid present in the dewatered hydrogenation mixture with a low molecular weight alcohol to obtain a first esterification mixture comprising carboxylic esters corresponding to the mono- and dicarboxylic acids;
 d) removing, in a first distillation, excess alcohol and low boilers from the first esterification mixture to obtain a bottom product;

e) separating, in a second distillation, the bottom product into an ester fraction depleted of 1,4-cyclohexanediols and a fraction comprising at least one 1,4-cyclohexanediol;

f) at least partly removing, in a third distillation, a stream comprising predominantly 6-hydroxycaproic ester from the ester fraction;

g) hydrogenating, in a second hydrogenation, employing a catalyst, the ester fraction from the third distillation from which 6-hydroxycaproic ester was removed at least partly, and distilling a product of the second hydrogenation to obtain 1,6-hexanediol; and h) heating the stream comprising predominantly 6-hydroxycaproic ester to temperatures greater than 200° C. under reduced pressure, to cyclize 6-hydroxycaproic ester to caprolactone, and distilling the caprolactone to obtain pure ε-caprolactone wherein the carboxylic acid mixture comprises:
adipic acid;
6-hydroxycaproic acid;
6-oxocaproic acid;
4-hydroxycyclohexanone;
formic acid;
and, based on a sum of adipic acid and hydroxycaproic acid, between 0.5 and 5% by weight of at least one 1,4-cyclohexanediol,
wherein the carboxylic acid mixture is obtained as a by-product of catalytic oxidation of cyclohexane to cyclohexanone/cyclohexanol with oxygen by water extraction of a reaction mixture.

2. The process of claim 1, wherein the catalyst for the first hydrogenation comprises ruthenium and wherein the catalyst is supported on shaped titanium dioxide or at least one activated carbon body.

3. The process of claim 2, wherein the catalyst for the first hydrogenation has a metal content in a range from 0.01 to 10% by weight based on total weight of the catalyst comprising at least a catalytically active metal and support, and a BET surface area in a range from 5 to 500 m$^2$/g measured to DIN 66 131.

4. The process of claim 1, wherein the first esterification is performed with at least one alcohol having 1 to 3 carbon atoms.

5. The process of claim 1, wherein the first esterification is performed with at least one alcohol having 4 to 10 carbon atoms.

6. The process of claim 1, wherein the first esterification is performed with methanol and, in the first distillation, a methyl carboxylate fraction essentially free of 1,4-cyclohexanediols is obtained at a top of a column, and a bottom fraction, comprising high boilers and at least one 1,4-cyclohexanediol, and the methyl carboxylate fraction is transferred into the third distillation.

7. The process of claim 1, wherein the first esterification is performed with n- or i-butanol and, in the first distillation, the at least one 1,4-cyclohexanediol are removed above a feed of a distillation unit such as a column with low boilers, and at least one butyl carboxylate are obtained as a sidestream or as bottoms comprising them and are transferred into the third distillation.

8. The process of claim 1, wherein the first and second distillations are performed in a single column.

9. The process of claim 6, wherein, in the first esterification, a fraction comprising at least one methyl dicarboxylate is removed in an upper side draw, a fraction comprising methyl 6-hydroxycaproate is removed as a lower side draw, and a fraction comprising 1,4-cyclohexanediols is removed as a bottom product.

10. The process of claim 8, wherein the first esterification employs n- or i-butanol, and wherein a fraction comprising butyl 6-hydroxycaproate is obtained in an upper side draw, a fraction comprising butyl dicarboxylate is obtained as a lower side draw, and a fraction comprising the at least one 1,4-cyclohexanediol is obtained as the top product.

11. The process of claim 1, further comprising:
at least partially reacting, in a second esterification analogous to the first esterification, the bottom product of the first distillation with further addition of the low molecular weight alcohol and of an esterification catalyst to obtain a second esterification mixture; and
further distilling, analogously to the first distillation, the second esterification mixture to obtain a second bottom product.

12. The process of claim 1, further comprising:
at least partially reacting, in a second esterification analogous to the first esterification, the ester fraction depleted of 1,4-cyclohexanediols resulting from the second distillation with further addition of the low molecular weight alcohol and of an esterification catalyst to obtain a second esterification mixture.

13. The process of claim 1, wherein the first esterification employs at least one catalyst.

14. The process of claim 1, wherein the second distillation stage yields an ester fraction depleted of 1,4-cyclohexanediols comprising less than 1% by weight 1,4-cyclohexanediols.

15. The process of claim 1, wherein the reduced pressure for heating the stream comprising predominantly 6-hydroxycaproic ester is between 300 and 20 mbar.

16. The process of claim 1, wherein the catalyst for the first hydrogenation comprises cobalt and wherein the catalyst is supported on shaped titanium dioxide or at least one activated carbon body.

17. The process of claim 1, wherein the catalyst for the first hydrogenation comprises nickel and wherein the catalyst is supported on shaped titanium dioxide or at least one activated carbon body.

18. The process of claim 1, wherein the dewatering employs a distillation apparatus.

19. The process of claim 1, wherein the first esterification is performed at a temperature between 70 and 300° C.

20. The process of claim 1, wherein heating the stream comprising predominantly 6-hydroxycaproic ester is performed in the presence of a second catalyst.

21. The process of claim 1, wherein the low molecular weight alcohol has 1-10 carbon atoms.

22. The process of claim 1, wherein the first esterification is performed without catalysts.

23. The process of claim 1, wherein the first esterification is performed with at least one homogeneous catalyst selected from the group consisting of sulfuric acid, phosphoric acid, hydrochloric acid, a sulfonic acid, p-toluenesulfonic acid, a heteropolyacid, tungstophosphoric acid, a Lewis acid, an aluminium compound, a vanadium compound, a titanium compound and a boron compound.

24. The process of claim 1, wherein the first esterification is performed with at least one heterogeneous catalyst selected from the group consisting of an acidic material, a superacidic material, an acidic $SiO_2$, an acidic $Al_2O_3$, an acidic $SnO_2$, an acidic $ZrO_2$, a superacidic $SiO_2$, a superacidic $Al_2O_3$, a superacidic $SnO_2$, a superacidic $ZrO_2$, a sheet silicate, and a zeolite, wherein the heterogeneous catalyst may be doped with at least one selected from the group consisting of a mineral acid, a sulphate and a phosphate, and/or an organic ion exchanger having at least one of sulfonic acid and carboxylic acid groups.

25. The process of claim 1, wherein the second hydrogenation is performed with at least one selected from the group consisting of copper, chromium, molybdenum, manganese, rhenium, ruthenium, cobalt, nickel and palladium.

26. The process of claim 1, wherein the cyclizing is performed without a catalyst.

27. The process of claim 1, wherein the cyclizing is performed with at least one homogeneous or heterogeneous catalyst selected from the group consisting of an alkali metal, an alkaline earth metal hydroxides, an alkaline earth metal oxide, an alkaline earth metal carbonate, an alkaline earth metal alkoxide, an alkaline earth metal carboxylate, an acid, sulfuric acid, phosphoric acid, an organic acid, sulfonic acid, a mono-carboxylic acid, a di-carboxylic acid, a salt of an acid, a Lewis acid and a Lewis base.

* * * * *